US007561281B2

(12) United States Patent
Drake, Jr.

(10) Patent No.: US 7,561,281 B2
(45) Date of Patent: Jul. 14, 2009

(54) SYSTEM AND METHOD FOR CONTROLLING TUBE THICKNESS

(75) Inventor: Thomas E. Drake, Jr., Ft. Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/142,073

(22) Filed: May 9, 2002

(65) Prior Publication Data

US 2002/0171846 A1 Nov. 21, 2002

Related U.S. Application Data

(63) Continuation-in-part of application No. 09/416,399, filed on Oct. 12, 1999, now Pat. No. 6,657,733.

(60) Provisional application No. 60/091,229, filed on Jun. 30, 1998.

(51) Int. Cl.
*G01B 9/02* (2006.01)
(52) U.S. Cl. ............................................ 356/502
(58) Field of Classification Search ................ 356/502, 356/432, 493–495
See application file for complete search history.

(56) References Cited

U.S. PATENT DOCUMENTS

| 3,911,733 A | 10/1975 | Bhuta et al. ................. 73/88 |
| 3,992,627 A | 11/1976 | Stewart ..................... 250/312 |
| 4,209,476 A * | 6/1980 | Harris ....................... 264/40.4 |
| 4,349,112 A | 9/1982 | Wilks et al. ................. 209/538 |
| 4,355,538 A | 10/1982 | Hall .......................... 73/811 |
| 4,388,830 A | 6/1983 | Narushima et al. ............ 73/579 |
| 4,393,711 A | 7/1983 | Lapides ...................... 73/592 |
| 4,422,177 A | 12/1983 | Mastronardi et al. ......... 378/17 |
| 4,541,280 A | 9/1985 | Cielo et al. .................. 73/603 |
| 4,803,639 A | 2/1989 | Steele et al. ................ 364/507 |
| 4,809,308 A | 2/1989 | Adams et al. ................ 378/99 |
| 4,841,460 A | 6/1989 | Dewar et al. ........... 364/571.02 |
| 5,014,293 A | 5/1991 | Boyd et al. .................. 378/197 |
| 5,065,630 A | 11/1991 | Hadcock et al. .............. 73/802 |
| 5,106,356 A * | 4/1992 | Rhodes et al. ................ 493/8 |
| 5,113,079 A | 5/1992 | Matulka ...................... 250/550 |
| 5,119,408 A | 6/1992 | Little et al. .................. 378/4 |
| 5,122,672 A | 6/1992 | Mansour ..................... 250/571 |
| 5,140,533 A | 8/1992 | Celette ....................... 364/559 |
| 5,295,073 A | 3/1994 | Celette ....................... 364/424 |

(Continued)

FOREIGN PATENT DOCUMENTS

GB 2 356 931 A 6/2001

OTHER PUBLICATIONS

NTIAC Newsletter; vol. 27, No. 5, Sep. 2002, 5 pp.

(Continued)

*Primary Examiner*—Hwa S Lee (Andrew)
(74) *Attorney, Agent, or Firm*—Bracewell & Giuliani LLP

(57) ABSTRACT

The invention is directed to a system and method for implementing process control for tubing thickness using sonic NDE techniques. The system may, for example, generate ultrasound waves in a test object during the manufacturing process. A detector such as an interferometer may be used to detect the ultrasound waves. An interpreter or analyzer may determine the tubing or sheet thickness from the waves. Then, a control system may determine and implement an appropriate control action on the process.

19 Claims, 5 Drawing Sheets

U.S. PATENT DOCUMENTS

| | | | |
|---|---|---|---|
| 5,319,567 A | 6/1994 | Ebenstein | 364/474.34 |
| 5,379,237 A * | 1/1995 | Morgan et al. | 703/2 |
| 5,384,717 A | 1/1995 | Ebenstein | 364/560 |
| 5,410,405 A | 4/1995 | Schultz et al. | 356/351 |
| 5,442,572 A | 8/1995 | Kiridena et al. | 364/560 |
| 5,490,195 A | 2/1996 | Berkley | 378/72 |
| 5,541,856 A | 7/1996 | Hammermeister | 364/552 |
| 5,552,984 A | 9/1996 | Crandall et al. | 364/424.03 |
| 5,574,226 A | 11/1996 | Reuther et al. | 73/669 |
| 5,608,166 A | 3/1997 | Monchalin et al. | 73/657 |
| 5,637,812 A | 6/1997 | Baker et al. | 73/865.6 |
| 5,672,830 A | 9/1997 | Rogers et al. | 73/597 |
| 5,724,138 A * | 3/1998 | Reich et al. | 356/492 |
| 5,760,904 A | 6/1998 | Lorraine et al. | 356/360 |
| 5,848,115 A | 12/1998 | Little et al. | 378/4 |
| 5,982,482 A | 11/1999 | Nelson et al. | 356/237.1 |
| 6,023,985 A | 2/2000 | Fournier | 73/865.6 |
| 6,047,041 A | 4/2000 | Ellinger | 378/58 |
| 6,057,927 A * | 5/2000 | Levesque et al. | 356/432 |
| 6,065,348 A | 5/2000 | Burnett | 73/801 |
| 6,078,397 A | 6/2000 | Monchalin et al. | 356/357 |
| 6,122,060 A | 9/2000 | Drake, Jr. | 356/359 |
| 6,128,081 A * | 10/2000 | White et al. | 356/503 |
| 6,182,512 B1 | 2/2001 | Lorraine | 73/655 |
| 6,205,240 B1 | 3/2001 | Pietrzak et al. | 382/152 |
| 6,220,099 B1 | 4/2001 | Marti et al. | 73/633 |
| 6,360,621 B1 | 3/2002 | Eldred et al. | 73/865.6 |
| 6,378,387 B1 | 4/2002 | Froom | 73/865.8 |
| 6,466,643 B1 | 10/2002 | Bueno et al. | 378/58 |
| 6,571,008 B1 | 5/2003 | Bandyopadhyay et al. | 382/154 |
| 6,637,266 B1 | 10/2003 | Froom | 73/583 |
| 2002/0171845 A1 | 11/2002 | Drake, Jr. | |
| 2002/0185240 A1 | 12/2002 | Drake, Jr. | |
| 2002/0186379 A1 | 12/2002 | Drake, Jr. | |

OTHER PUBLICATIONS

Froom, Douglas A., et al.; Solving Problems with Advanced Technology, 1999 IEEE, 4 pp.

Alkire, M.G., Department of the Air Force Memo regarding Construction Project Data; May 7, 1982, Bates 000010 through Bates 000068.

U.S. Air Force, Military Construction Project Data, Apr. 14, 1982, Bates 000074 through Bates 000129.

U.S. Air Force, Attachment I to Request for Environmental Impact Analysis, Dec. 2, 1982, Bates 000130 through Bates 000167.

Stanghellini, Frank D., Department of the Air Force Memo regarding Criteria Changes, Jan. 9, 1985, Bates 000168 through Bates 000214.

Metro Today, The Sacramento Union; May 12, 1983, Bates 000215 through Bates 000216.

Letter Contract Between Department of the Air Force and Par Systems Corp., Aug. 3, 1984, Bates 000217 through Bates 000312.

Timeline and Equipment List for Contract Between Department of the Air Force and Par Systems Corp., Aug. 3, 1984, Bates 000313 through Bates 000325.

Spacemaker, Jun. 19, 1997, Bates 000326 through 000327.

Civilian Personnel Position Description, Department of the Air Force; Jul. 10, 1989, Bates 000328 through Bates 000332.

Aviation Week & Space Technology, Mar. 13, 1989, Bates 000333 through Bates 000336.

UltraOptec, Laser Ultrasonic System, 1999 IEEE, Bates 000337 through Bates 000340.

J.W. Bader, et al., Laser Ultrasonics or Alternative NDI Composite Defect, Nov. 20, 1990, Bates 000342 through Bates 000446.

Douglas A. Froom, Statement of Work for Advanced Ultrasonic Component Inspection System, Jul. 14, 1993, Bates 000447 through 000490.

Award of Contract from Department of the Air Force, Aug. 11, 1993, Bates 000491 through Bates 000492.

UltraOptec, LUIS Phase 3 Acceptance Test Report, Feb. 16, 1996, Bates 000493 through Bates 000501.

Spacemaker, Feb. 22, 1996, Bates 000502.

PCT International Search Report; European Patent Office; Feb. 6, 2004; 9 pages.

http://metwww.epfl.ch/Brillouln/physique_brillouinE.thm; "Physics of Brillouin scattering"; Mar. 26, 2002; 3 pages.

Using Light to Measure Temperature and Strain; Report No. 6; date unknown; 4 pages.

"Temperature and annealing dependence of the longitudinal ultrasonic velocity in aluminum alloys"; Johnson, Ward et al.; J. of Mater. Res., vol. 8, No. 7, p. 1558; 1996.

http://nte-serveur.univ-lyon1.fr/nte/spectroscopie/resumESOPS/Alig1.htm; "Ultrasonic spectroscopy For characterization of Polymeric Materials"; I. Alig and D. Lellinger; Mar. 26, 2002; 2 pages.

"Temperature Dependence of Ultrasonic Velocity Using Diffuse Fields; Implications for Measurement of Stress"; Richard Weaver and Oleg Lobkis; Department of Theoretical and Applied Mechanics; University of Illinois; reprint QNDE 2000; 8 pages.

* cited by examiner

SYSTEM AND METHOD FOR CONTROLLING TUBE THICKNESS

RELATED APPLICATIONS

This application claims the benefit of, incorporates by reference, and is a Continuation-In-Part of Non-Provisional patent application Ser. No. 09/416,399 filed on Oct. 12, 1999, now U.S. Pat. No. 6,657,733 entitled "METHOD AND APPARATUS FOR DETECTING ULTRASONIC SURFACE DISPLACEMENTS USING POST COLLECTION OPTICAL AMPLIFICATION" to Thomas E. Drake. Non-Provisional patent application Ser. No. 09/416,399 in turn claims benefit to U.S. Provisional Application No. 60/091,229 filed on Jun. 30, 1998. This application incorporates by reference the prior U.S. Provisional Application No. 60/091,240 filed on Jun. 30, 1998 entitled "METHOD AND APPARATUS FOR ULTRASONIC LASER TESTING" to Thomas E. Drake. This application is related to and incorporates by reference: Non-Provisional patent application Ser. No. 10/142,072, filed on May 9, 2002, entitled "SYSTEM AND METHOD FOR ON-LINE CONTROL OF PAPER ELASTICITY AND THICKNESS" to Thomas E. Drake; Non-Provisional patent application Ser. No. 10/142,071, filed on May 9, 2002, entitled "SYSTEM AND METHOD FOR CONTROL OF PAINT THICKNESS" to Thomas E. Drake, and Non-Provisional patent application Ser. No. 10/142,178, filed on May 9, 2002, entitled "SYSTEM AND METHOD FOR CONTROLLING WAFER TEMPERATURE".

TECHNICAL FIELD OF THE INVENTION

This invention relates in general to non-destructive examination techniques. More specifically, the invention relates to control of steel tubing manufacturing using ultrasound testing methods for determining wall thickness.

BACKGROUND OF THE INVENTION

Non-destructive examination (NDE) of objects may be used to test for defects in manufactured parts. NDE provides a method of examination that limits damage the tested part. As such, parts may be examined before they are placed in service. Further, used parts may be examined for flaw or defects resulting from use.

However, many typical NDE techniques are slow. Further, the results of the tests are difficult to interpret and typically require an human observer. Typically, these techniques require a human observer to perform analysis. Therefore, the techniques is not automated.

These typical techniques may also require contact with the surface of the tested part. In many processes, parts or objects are moving through the process at great speeds. In other processes, contact with the part or object may be limited because of surface temperature and/or drying or annealing surface films. Further, contact with the part may be limited by other process variables.

As such, these techniques are not suitable for use in process control. The slow testing time may not provide enough information for process control applications. Further, a lack of automation in the analyzing the results limits applicability to process control. In addition, contact with the part may not be suitable, preventing the technique from use in the process.

For example, in the manufacturing of tubing, a tube may be hot (1000° C.) and may be rotating about and/or translating along an axis. As such, typical methods that require contact with the part may not be suitable.

As such, many typical NDE techniques suffer from deficiencies in speed and automation. Many other problems and disadvantages of the prior art will become apparent to one skilled in the art after comparing such prior art with the present invention as described herein.

SUMMARY OF THE INVENTION

Aspects of the invention may be found in an apparatus for determining the thickness of tubing walls. The apparatus may have a sonic energy generator, one or more detectors and an interpreter. The sonic energy generator may, for example, be a laser generator directing a beam of coherent electromagnetic energy at an object. From the impinging energy, sonic energy waves may be generated about the object or along the surface of the object, among others. The one or more detectors may detect and/or measure the sonic energy waves. An interpreter may then be used to determine the tube thickness.

Aspects of the invention may also be found in a method for determining tube thickness. Sonic energy waves may be generated about a test object using a sonic energy generator. The sonic energy waves may be detected and/or measured by a sonic energy detector. The tube thickness may be determined by an interpreter.

Another aspects of the invention may be found in an apparatus for process control of tube thickness. The apparatus may have a sonic energy generator, one or more detectors, and a control system. The sonic energy generator may, for example, be a laser generator directing a beam of coherent electromagnetic energy at an object. From the impinging energy, sonic energy waves may be generated about the object or along the surface of the object, among others. The one or more detectors may detect and/or measure the sonic energy waves. The control system may determine what action may be taken to achieve and/or maintain an aspect of the object near or about a set point.

A further aspects of the invention may be found in a method for process control of tube thickness. Sonic energy waves may be generated about a test object using a sonic energy generator. The sonic energy waves may be detected and/or measured by a sonic energy detector. An action may be determined, which may achieve and/or maintain an aspect of the object near or about a set point.

Another aspects of the invention may be found in a control system. The control system may have an analyzer, a controller, and interfaces. An interface may receive data from a sonic energy detector. The analyzer may determine and/or generate a signal relating to the tube thickness. The controller may use the signal from the analyzer to determine an appropriate control action. The action may be implemented using an interface to the process. Furthermore, the control system may have one or more modelers, one or more stored results, one or more threshold values, and one or more algorithms. Each of these may or may not be used by the analyzer or controller in performing their respective function.

As such, a system for control of a tubing manufacturing process is described. Other aspects, advantages and novel features of the present invention will become apparent from the detailed description of the invention when considered in conjunction with the accompanying drawings.

BRIEF DESCRIPTION OF THE DRAWINGS

For a more complete understanding of the present invention and advantages thereof, reference is now made to the following description taken in conjunction with the accompanying drawings in which like reference numbers indicate like features and wherein.

Corresponding reference numerals indicate corresponding parts throughout the several views of the drawings.

DETAILED DESCRIPTION OF THE PREFERRED EMBODIMENT

Sonic energy traverses through objects with varying characteristics. These characteristics may include speed, velocity, wave type, frequency spectrum, amplitude. Further the sonic energy may partially reflect from surfaces or inconsistencies. Waves may also translate across a surface.

The characteristics of the sonic energy may be a function of various aspects of the substance about which the sonic energy travels. These aspects may include elasticity, internal structure, flaws, thickness of material, and layers of film, among others. These aspects may be a further function of temperature, and composition. As such, sonic energy waves may be used to aid in determining aspects of the material for use in process control.

For example, the thickness of an object may be determined by generating and measuring ultrasound waves about the object. The measured thickness may then be used to control the process. In one exemplary embodiment, the thickness of tubing may be determined with a laser generated ultrasound system. The thickness may then be used to vary parameters associated with the process such as process temperature, torque, rotation speed, translation speed, and pressure, among others.

Figure 1:
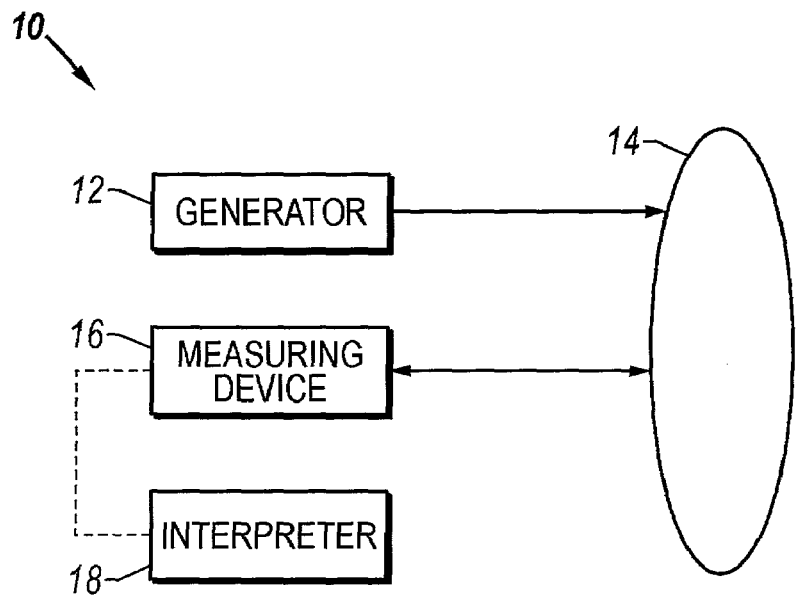
FIG. 1 is a schematic block diagram the system, according to the invention.

FIG. 1 depicts a system, according to the invention. In the system 10, a sonic energy generator 12 may generate sonic energy waves in a test object 14. The system may also have a detector or measuring device 16. The detector or measuring device 16 may detect or measure the sonic energy waves. An interpreter 18 may be used to determine the sonic wave characteristic, material aspect and/or value of a variable from which the material aspect depends.

The sonic energy generator 12 may take various forms. These forms may include a coherent electromagnetic energy source, a laser, a plasma generator, and a transducer, among others. Further, the coherent electromagnetic energy source and/or laser may take various forms. These forms may include a $CO_2$ laser, a q-switch YAG laser, a mid-IR laser, and other solid-state and/or gas lasers, among others. However, various lasers may be envisaged.

The measuring device 16 may take various forms. These forms may include an interferometer, a gas-coupled laser acoustic detector, and a transducer, among others. Further, the interferometer may take the form of a Mach-Zender, Fabry-Perot, Dual Differential Confocal Fabry-Perot, Two Wave Mixing, photorefractive or other interferometer. Other interferometers and sonic energy detection methods may be used as well. A laser may be used to generate coherent electromagnetic energy for use in the interferometer. One exemplary embodiment is a long pulse ND:YAG laser. However, other lasers may be used.

The interpreter 18 may take various forms. These forms may include a computer, workstation, handheld, computational circuitry, analog device, or digital alarm, among others. Further, the interpreter may compare the signal to an expected signal, determine the location of one or more peaks, determine the amplitude of one or more peaks, and transform the signal, among others. The interpreter may operate on the signal in a time domain or frequency domain, among others. Further, the interpreter may determine the thickness of tubing or a metal sheet by comparing the timing of reflected peaks. The interpreter may also use data from other process parameters or measurements in determining the thickness. These other process parameters may include distance between generation and measurement, temperature, rotational and/or translational velocity, and composition, among others.

In one exemplary embodiment, the system may take the form of a laser ultrasound system. The laser ultrasound system may use a $CO_2$ laser. A beam from the laser may be direct to the object. This beam may be directed through fiber optic cable. A ND:YAG laser may direct a beam of coherent electromagnetic energy toward the object. The beam may, at least in part, reflect from the object with an altered characteristic indicative of the sonic energy. Part of the reflected beam may be collected by the collection optics of a dual differential confocal Fabry-Perot interferometer. However, a photorefractive, two wave mixing, or other interferometer may be used.

In this exemplary embodiment, the interferometer may generate a signal. The signal may be interpreted by the interpreter or analyzer. From the signal, the interpreter or analyzer may determine the thickness of the tubing or sheet.

Figure 2:
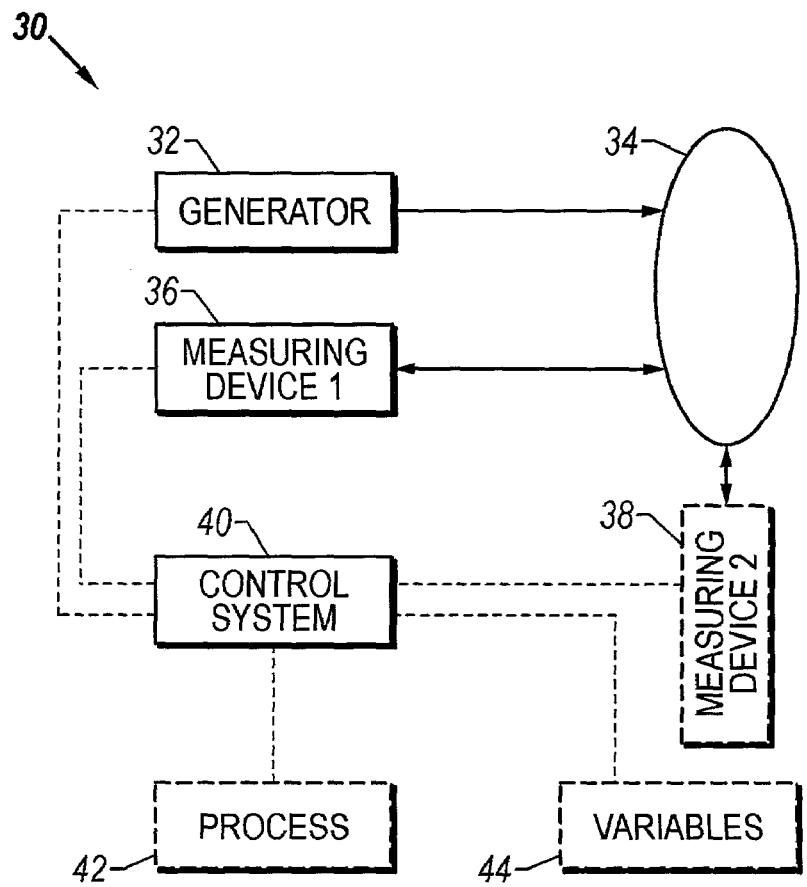
FIG. 2 is a schematic block diagram of the system, according to the invention.

FIG. 2 is a schematic block diagram of a system, according to the invention. The system 30 may have a generator 32, one or more measuring devices 36 and 38, and a control system 40. The control system 40 may or may not be coupled to generator 32 and the one or more measuring devices 36 and 38. The system 30 may or may not also be coupled to the process 42 and other variables 44. However, various configurations may be envisaged. These elements may be together, separate, or in various combinations, among others.

The generator 32 may generate sonic energy waves in the object 34. The one or more detectors 36 and 38 may detect the sonic energy waves. The control system 40 may receive signals from the one or more detectors 36 and 38. From the signals, the control system 40 may determine an appropriate control action. Further, the control system 40 may implement the control action. The control action may include manipulating characteristics associated with the generator, altering characteristics associated with the measuring device, and manipulating process parameters, among others. The control system may also use other process measurements, parameters, and variables 44 in determining the control action.

The generator 32 may take various forms. These forms may include a coherent electromagnetic energy source, a laser, a plasma generator, and a transducer, among others. Further, the coherent electromagnetic energy source and/or laser may take various forms. These forms may include a $CO_2$ laser, a q-switch YAG laser, a mid-IR laser, and other solid-state and/or gas lasers, among others. However, various lasers may be envisaged.

The one or more measuring devices 36 and 38 may take various forms. These forms may include an interferometer, a gas-coupled laser acoustic detector, and a transducer, among others. Further, the interferometer may take the form of a Fabry-Perot, Dual Differential Confocal Fabry-Perot, Two Wave Mixing, photorefractive or other interferometer. Other interferometers and sonic energy detection methods may be used as well. A laser may be used to generate coherent electromagnetic energy for use in the interferometer. One exemplary embodiment is a long pulse ND:YAG laser. However, other lasers may be used.

The control system 40 may take various forms. These forms may include a digital control, analog control, or distributed control system, among others. Further, the control system 40 may or may not be implemented on a computational circuitry, computer, or workstation, among others. However, each of these elements may be utilized in various combinations.

The variables 44 may take various forms. These forms may include known process parameters, other measured values, control parameters, model parameters, algorithm parameters, and set points, among others.

For example, a generating laser may direct a beam at a tube or sheet of metal. The beam may impinge on the surface of the tube or sheet, generating ultrasonic waves. A measuring beam may be directed at the tubing or sheet. The measuring beam may reflect with a characteristic associated with the ultrasonic waves. The reflected beam may be collected in an interferometer. The interferometer may generate a signal associated with the ultrasonic waves. The signal may be received by a control system.

The control system may determine the thickness and/or determine an appropriate control action. These control actions may take various forms. For example, the control actions may to alter the rotational and/or translation velocity of the tubing. The control action may also be to alter the temperature, pressure, or torque, among others, associated with the process. Further, the control action may be to alter the behavior of the measuring devices and/or generating laser. For example, the control action may cause the measuring beam and/or collector to follow the spot at which the generating beam hit.

In addition, the control system may use other variables in determining the control action. For example, the control system may use information associated with the rotational and/or translation velocity of the tubing. Alternately, the control system may use the temperature. However, various actions and variables may be envisaged.

Figure 3:
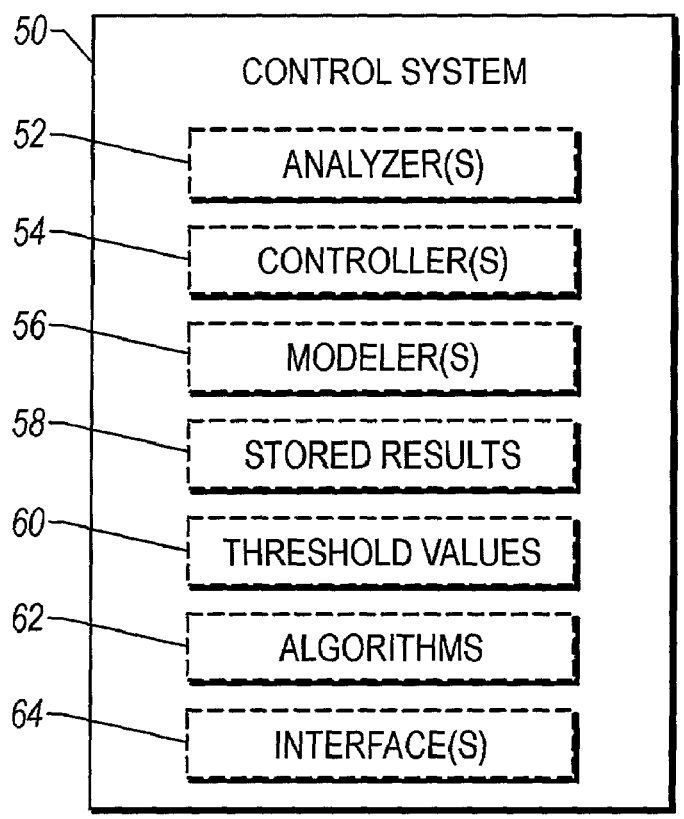
FIG. 3 is a block schematic diagram of an exemplary embodiment of a control system as seen in FIG. 2.

FIG. 3 is a block diagram of an exemplary embodiment of a control system for use in the system as seen in FIG. 2. The control system 50 may have analyzers 52, controllers 54, modelers 56, stored results 58, threshold values 60, algorithms 62, and interfaces 64. However, the control system may have some, all, or none of these elements. Further, these elements may be separate, together, or in various combinations, among others.

The analyzer 52 may perform various functions. These functions may include estimating parameters, determining location and/or amplitude of peaks, comparing location and/or amplitude of peaks to a value, and/or comparing the signals to expected signals. Further the analyzer 52 may perform these functions in time domain and/or frequency domain. In addition, the analyzer may utilize the output of the process, other variables, the modeler 56, stored results 58, and threshold values 60, among others.

The controller 54 may perform various functions. These functions may include determining an action in response to an output from the analyzer 52. The action may relate to manipulating process parameters, generator parameters, measuring device parameters, and other variables, among others. Further, the action may be an alert, alert, or message, among others. In addition, the controller 54 may utilize values of process and other variables in determining a control action.

The modeler 56 may take various forms. These forms may include a CAD model, a propagation model, and a control model, among others. Further, the model may use parameters and other outputs from the process, other variables, stored results, threshold values, process setting, and set points, among others, in performing its function. In addition, the model may interact with the controller 54 and/or the analyzer 52, to aid in the function of those units.

The stored results 58 may take various forms. These forms may include previous results, process data, expected results, modeler 56 output, analyzer 52 output, controller 54 output, and user data, among others. The stored results may or may not be accessed by the process, controller 54, analyzer 52, and modeler 60, among others.

The threshold values 60 may be used in various manners. These manners may include for comparison with peaks, set points, model output, process parameters, and other variables, among others. Further, these threshold values 60 may be determined automatically or set by a user.

The algorithms 62 may direct the performance of various functions. These functions may include controller, generator, measuring device, and process functionality, among others.

The interfaces 64 may take served to communicate with various devices. These devices may include the process, generator, measuring devices, other equipment, network interfaces and user interfaces, among others.

For example, the control system may receive a signal from one or more measuring devices associated with ultrasound waves in tubing. The analyzer may determine a parameter associated with the thickness of the tubing. The analyzer may use information associated with temperature, and velocity, among others, in determining the thickness. Further, the analyzer may utilize the output of a propagation model or an expected result in determining the thickness. For example, the analyzer may compare a time-domain location of a peak to an expected result or an output of a wave propagation model. Alternately, the analyzer may regress a parameter associated with thickness from the data and a propagation model.

The analyzer may provide a signal to the controller. The controller may then determine a control action. The controller may then implement the control action through the interfaces. For example, the controller may manipulate a process parameter. Alternately, the controller may alter the firing of the generation laser or the tracking of a measuring device.

Figure 4:
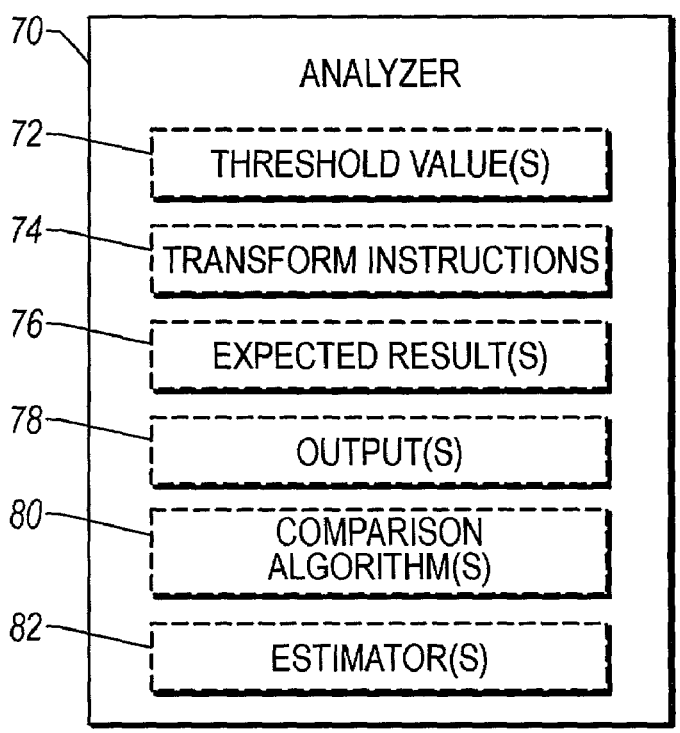
FIG. 4 is a block schematic diagram of an exemplary embodiment of an analyzer as seen in FIG. 3.

FIG. 4 is a block diagram of an exemplary embodiment of an analyzer for use in the controller of FIG. 3. Further, the analyzer may act as an interpreter as seen in FIG. 1. The analyzer 70 may or may not have threshold values 72, transform instructions 74, expected results 76, outputs 78, comparison algorithms 80, and estimators 82. However, the analyzer 70 may have all, some, or none of the elements. Further, these elements may be separate, together, or in various combinations, among others.

The analyzer may receive data from other components in the control system, the measuring devices, process, or other variables, among others. The analyzer may function to analyze these signals together, separately, or in various combinations.

The transform instructions 74 may direct the implementation of various functions. These forms may include scaling and Fourier transforms, among others.

The expected results 76 may take various forms. These forms may include an expected time domain sonic wave, a frequency domain sonic wave response, a location of one or more peaks in a time domain and/or frequency domain data, an amplitude of one or more peaks in a time domain and/or frequency domain data, the output of a wave propagation model, a past result, and expected parameters of a model, among others. However, other expected results may be envisaged.

The comparison algorithms may implement various functions. These functions may include comparison between the signal and an expected result or threshold values. The comparison may be performed in a frequency and/or time domain, among others. Further, these functions may include comparing peak amplitudes with an expected amplitude or threshold value, subtracting an expected result from a signal, and compare an parameter determined by the estimator 82 to a threshold or expected value, among others.

The estimator 82 may function to determine parameters associated with the data from the one or more measuring devices. For example, the estimate may fit a line or some other curve to the data. The estimator 82 may, alternately, regress parameters of a model from the data. Further, the estimator 82 may use various methods and algorithms for fitting and/or regressing. Further, the estimator 82 may use signals and inputs from the control system, process, measuring devices, generator, and other variables, among others, in regressing the parameters.

The outputs 78 may be outputs to other components of the control system. For example, the outputs may direct the results of the comparison algorithms 80, estimators 82, or transform instructions 74, among others, to other components of the control system such as the modeler, controller, interfaces, stored results, or other analyzers, among others.

For example, the analyzer may receive signals from one or more measuring devices. These signals may be compared to an expected signal. Alternately, the location or amplitude of the peaks may be compared to a threshold value, an expected value, or a model output. Further, the signals may be used in regressing a parameter associated with tubing thickness. The regression may utilize a modeler. The analyzer may then send an output signal to a controller. The controller may determine a control action.

Figure 5:
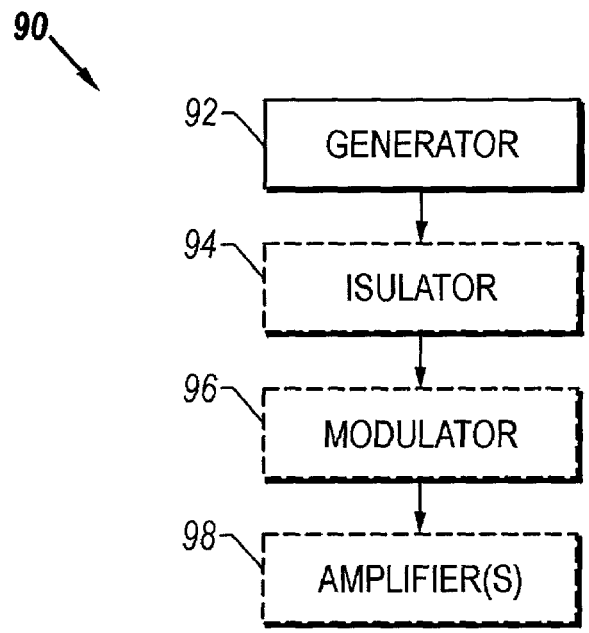
FIG. 5 is a schematic block diagram of an exemplary embodiment of the generator as seen in FIG. 1.

FIG. 5 is an schematic block diagram of an exemplary embodiment of a laser as seen in FIG. 1 and FIG. 2. The laser 90 may be used as a sonic energy generator or a beam generator for an interferometer, among others. The laser 90 may, for example, have a pulse generator 92 that generates a pulse. The pulse may traverse an isolator 94, a modulator 96, and one or more amplifiers 98. However, these elements may or may not be included. Further, these elements may be separate, together, or in any combination, among others.

The pulse generator 92 may take various forms. These forms may include those described above, among other. The isolator 94 may function to prevent backscattering of light into the pulse generator.

The modulator 96 may take various forms. These forms may include electro-optic modulators, and acousto-optic modulators, among others. Further, the modulator 96 may function to alter wave characteristics such as pulse length, pulse frequency profile, phase and pulse amplitude, among others. This function may or may not be implemented in conjunction with the amplifiers 98.

The amplifiers 98 may take various forms. These forms may include pumped slabs, cylinders, and zigzag slabs, among other. The amplifiers may function to increase the amplitude of the laser pulse. In addition, the amplifiers may be configured to alter other wave characteristics such as frequency profile, and pulse length, among others.

Figure 6:
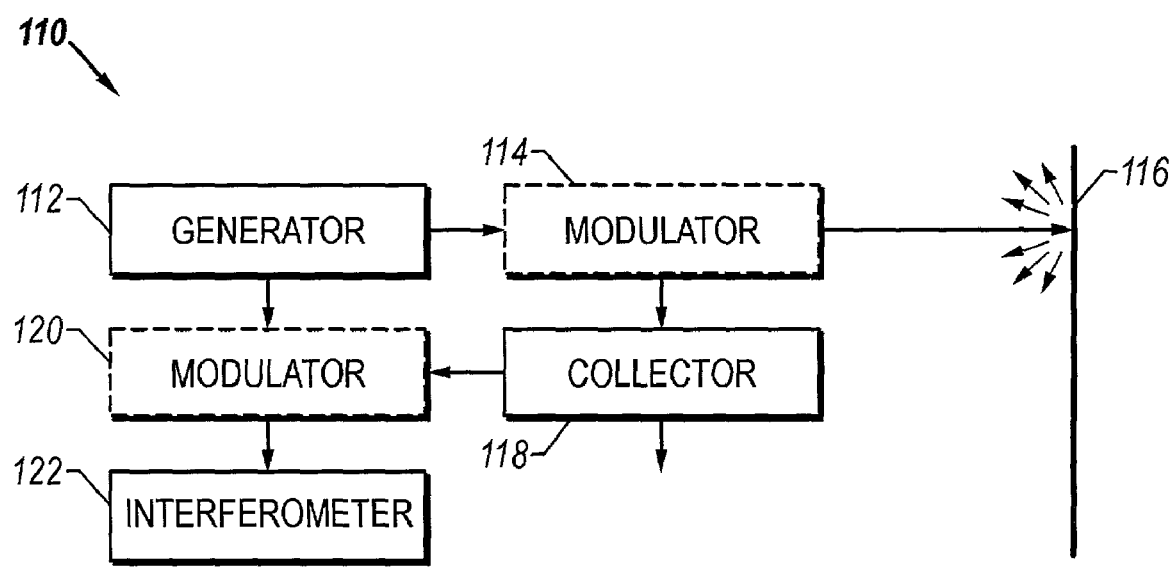
FIG. 6 is a schematic block diagram of an exemplary embodiment of a measuring device as seen in FIG. 1.

FIG. 6 is a schematic block diagram of a exemplary embodiment of a measuring device or detector as seen in FIGS. 1 and 2. The measuring device 110 may have a generator 112, a modulator 114, a collector 118, a modulator 120, and an interferometer. These elements may or may not be included. Further, these elements may be together, separate, or in various combinations, among others.

The generator 112 may generate a coherent electromagnetic energy beam. The beam may or may not be modulated with modulator 114. The beam may be directed to an object 116. A modulated beam may reflect from the object 116 with a characteristic associated with sonic energy waves about the object 116. Part of the modulated beam may be collected in a collector 118. The collected beam may or may not be directed to a modulator 120. The beam may be directed to an interferometer 122 wherein the beam may be detected and measured.

The generator 112 may take various forms. These forms may include a coherent electromagnetic energy source or a laser, among others. Further, the coherent electromagnetic energy source and/or laser may take various forms. These forms may include a $CO_2$ laser, a q-switch YAG laser, a mid-IR laser, an ND:YAG laser and other solid-state and/or gas lasers, among others. However, various lasers may be envisaged.

The modulator 114 may take various forms. These forms may include electrooptic modulators, and acousto-optic modulators, among others. Further, the modulator 114 may alter a characteristic of the beam such as frequency profile, pulse length, phase and pulse amplitude. This function may be performed in conjunction with an amplifier. For example, the modulator 114 may alter the wave characteristic to enhance reflection, compensate for beam attenuation, and compensate for Doppler effects relating to object movement or a scanning motion, among others.

The collector 118 may function to collect part of the reflected modulated beam. The collector may have various apertures.

The modulator 120 may take various forms. These forms may include electro-optic modulators, and acousto-optic modulators, among others. Further, the modulator 114 may alter a characteristic of the beam such as frequency profile, pulse length, phase and pulse amplitude. For example, the modulator 114 may alter the wave characteristic to enhance detection, compensate for beam attenuation, and compensate for Doppler effects relating to object movement or a scanning motion, among others.

The interferometer 122 may take various forms. These forms may include those listed above, among others. These forms may include a Fabry-Perot, dual differential confocal Fabry-Perot, two wave mixing, and photo-refractive interferometer, among others. The interferometer may send a signal relating to the sonic energy wave to an analyzer, control system, or interpreter, among others.

In one exemplary embodiment, a ND:YAG laser may generate a beam. The beam may be directed at a surface of a tube. The beam may reflect from the surface with an characteristic associated with an ultrasonic signal. For example, the ultrasonic signal may have been generated and reflected from other surfaces associated with the tubing. In this manner, the ultrasonic signal may be indicative of tubing thickness. The reflected beam may be collected by a collector and directed to an interferometer. Intermediately, the beam may or may not pass through a modulator. The interferometer may generate a signal associated with the ultrasonic signal and direct the signal to a control system.

Figure 7:
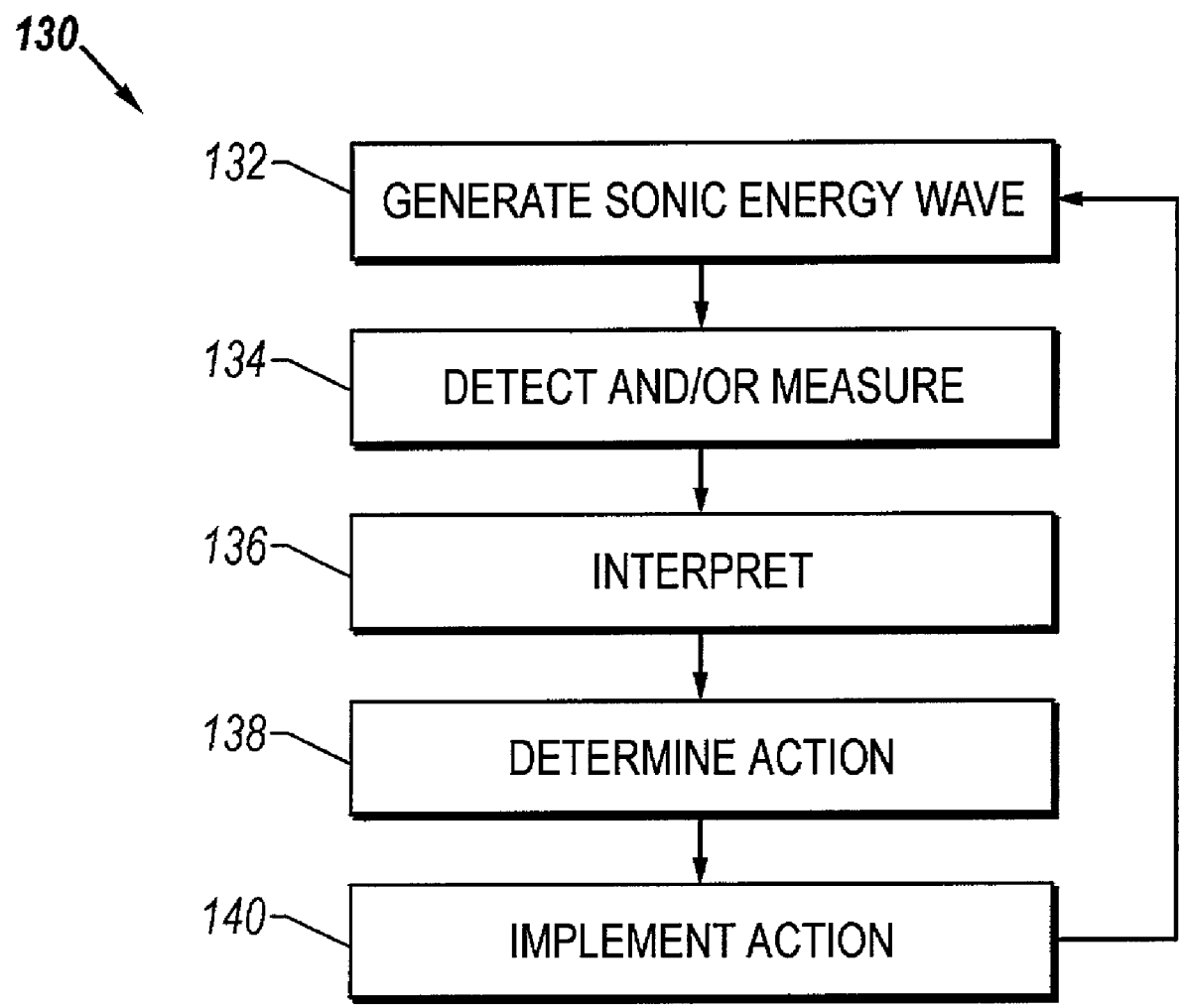
FIG. 7 is a block flow diagram of an exemplary method for use by the system of FIG. 2.

FIG. 7 is a block flow diagram of an exemplary method for use by the system as seen in FIG. 2. In the method 130, a sonic energy wave may be generated about a test object as seen in a block 132. The sonic energy wave may, for example, be generated by directing a beam of coherent electromagnetic energy at the object. However, various means of generating sonic energy waves may be envisaged.

As seen in a block 134, the sonic energy wave may be detected and/or measured by a measuring device. For example, the sonic energy wave may be measured with an interferometer. However, various methods for measuring sonic energy waves may be envisaged.

An interpreter or analyzer may interpret a signal from the measuring device as seen in a block 136. The interpreter or analyzer may use various methods to determine a result. These methods may include regression of parameters from data, determination of the location or amplitude of a peak, and/or comparison of the location or amplitude of the peak to a threshold value, among others. The analysis may be performed on time domain or frequency domain data. In addition, the analysis may utilize generator parameters, object parameters, measurement device parameters, process measurements, and/or process variables, among others.

From the interpretation, a controller or control system may determine an action as seen in a block 138. This action may be to alter a parameter associated with the process. Alternately, the action may relate to the sonic generator, the measurement device, or other process variables. The control system may implement the action as seen in a block 140. For example, the action may be to alter the torque, rotational and/or translation velocity, pressure, and/or temperature in the process. In another example, the action may be to alter the frequency of a laser beam to compensate for beam attenuation, Doppler distortion, or noise, among others. In a further example, the action may be to alter a characteristic of measuring device. Further, the action may be an alarm or alert. However, various actions may be envisaged.

For example, a sonic energy signal may be generated in the tubing with a generating beam. The sonic energy signal may reflect from various surfaces in the tubing. A measuring beam may be directed at the tubing and reflect with a modulation associated with the sonic energy signal. The reflected beam may then be collected and directed to a interferometer. The interferometer may direct as signal associated with the sonic energy signal to a control system. In the control system, a parameter associated with tubing wall thickness may be determined by an analyzer. The parameter may be used to determine a control action by a controller. The control action may be to change the torque, velocity, pressure, and/or temperature associated with the tube manufacturing process.

Figure 8:
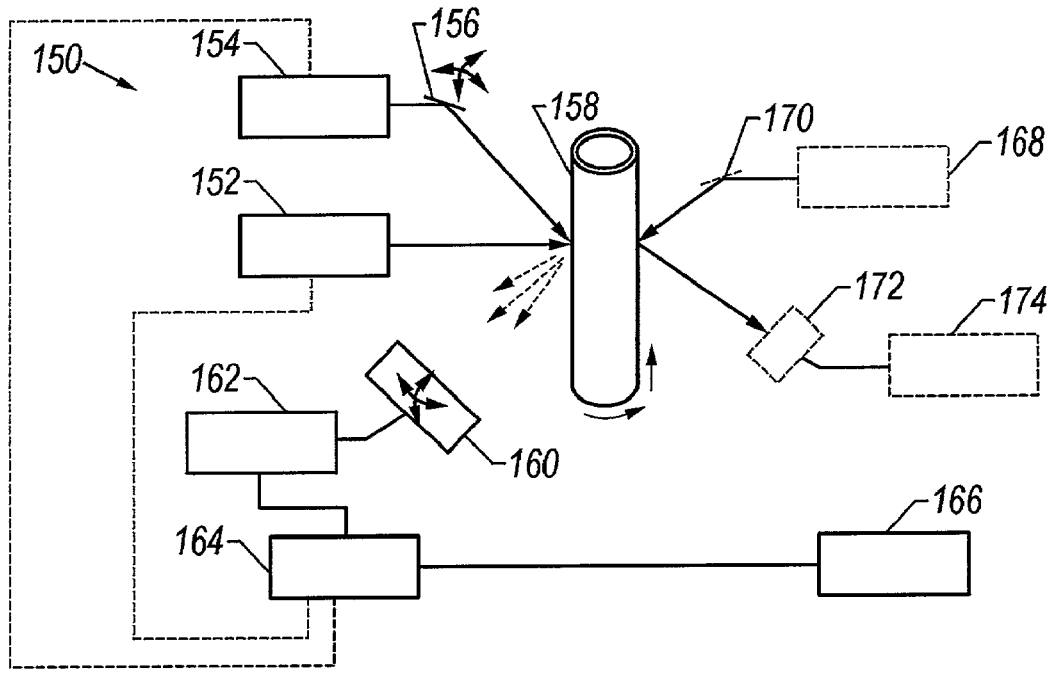
FIG. 8 is a schematic block diagram of an exemplary embodiment of the system as seen in FIGS. 1 and 2.

FIG. 8 is a schematic block diagram of an exemplary embodiment of the system as seen in FIGS. 1 and 2. In this exemplary embodiment 150, a laser generator 152 directs a beam at a tubing outer surface. The beam imparts energy to the surface and generates an ultrasonic signal. The ultrasonic signal may reflect form an inside surface of the tube and manifest an alteration of the outer surface. A measuring beam from a measuring beam generator such as an ND:YAG laser may be direct to the outer surface of the tubing by a mirror 156. The mirror may rotate in various angles. Further the mirror may or may not direct the measurement beam to follow a single location on the surface of the tubing. The single location on the surface may or may not be the same location as was impinged by the generating beam. In this manner, the mirror may compensate for the movement of the tubing. The measuring beam may reflect with a characteristic associated with the sonic energy signal and be collected in a collector 160. The collector 160 may or may not also rotate to follow a location on the surface.

The collector 160 may then direct the collected beam to an interferometer 162. The interferometer may generate a signal indicative of the sonic energy signal and direct the generated signal to a control system 164. The control system 164 may then determine a control action to be performed on the process 166. In addition, the control system 164 may control the behavior of the laser generator 152, the measurement laser 154, the mirror 156, the collector 160, and the interferometer 162, among others. In addition, the control system may use parameters associated with the process 166 in determining the control action.

Further, a second measurement system with a measurement laser 168, mirror 170, collector 172, and interferometer 174, among others. The mirror 168 and collector 172 may also function to follow a single location on the surface. Alternately the beam may be directed to another location or a location through which the surface of the pipe moves. The analyzer may use information associated with the location of the impinging of the measuring beam in determining the thickness of the tubing. However, various configurations may be envisaged. Further, these elements may be separate, together or in various combinations, among others.

Figure 9:
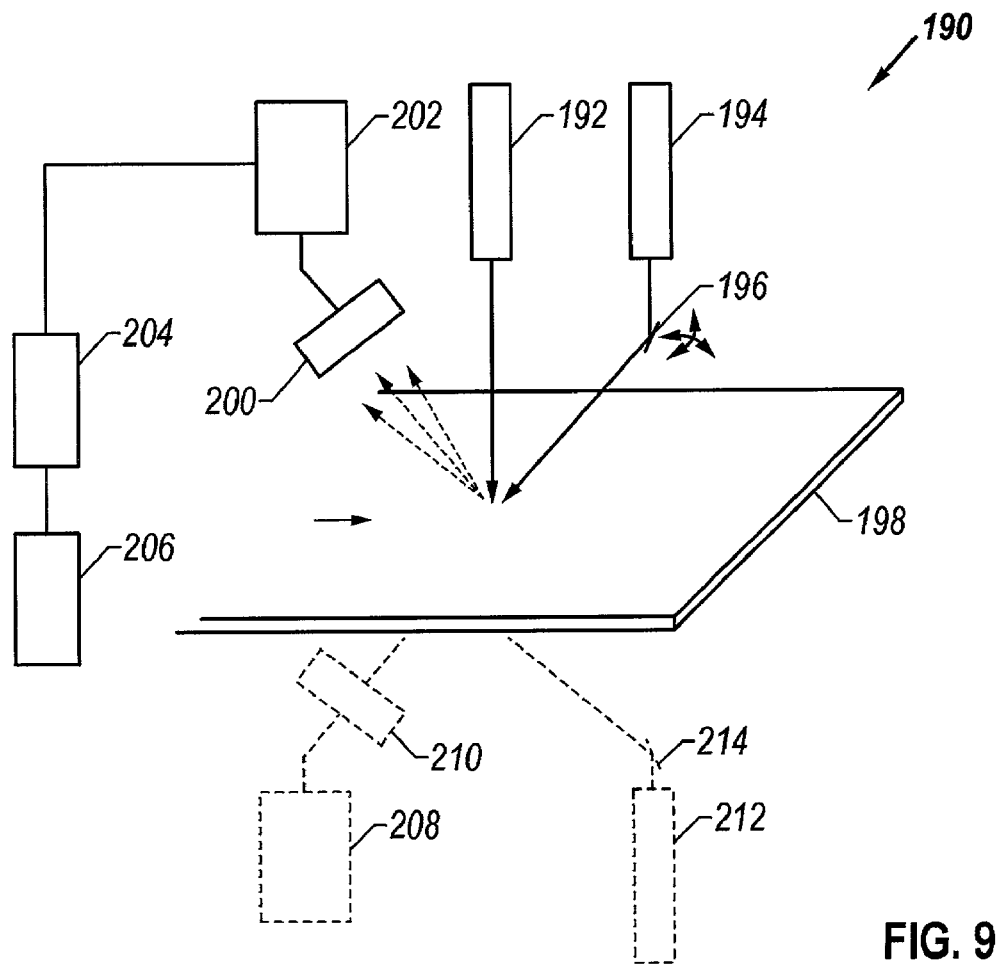
FIG. 9 is a schematic block diagram of an exemplary embodiment of the system as seen in FIGS. 1 and 2.

In another exemplary embodiment, the system may be used in controlling a sheet making process. FIG. 9 is a schematic block diagram of a exemplary embodiment of the system as seen in FIGS. 1 and 2. In the exemplary embodiment 190, a generating laser 192 directs a beam to the surface where the beam imparts energy and generates a sonic energy signal. A measuring beam may be generated by a generator 194, such as a ND:YAG laser. The measuring beam may be directed to a location on the surface of the sheet be a rotating mirror 196. The rotating mirror 196 may function to direct the beam to the same or different location on the surface of the sheet. In this manner, the mirror may compensate for the motion of the sheet and/or maintain a constant or know distance between the generation location and the measurement location.

The measurement beam may reflect from the surface with a characteristic associated with the sonic energy signal. The reflected beam may be collected by a collector 200. The collector 200 may also rotate to follow the location on the surface. The collected beam may then be directed to an interferometer 202. The interferometer 202 may generate a signal associated with the sonic energy signal. The generated signal may be directed to a control system 204.

The control system 204 may use the signal and/or other process parameters and measurements to determine a control action. The control action may take various forms including altering the process velocity, pressure, and temperature, among others. In addition, the control system may control the lasers 192 and 194, the mirror 196, the collector 200, and the interferometer 202. However, various control actions may be envisaged.

The system 190 may also have a second measuring device with a laser 212, a mirror 214, a collector 210, and an interferometer 208, among others. The second measuring device may or may not be on an opposite side of the sheet. Further the mirror 214 may direct to the measuring beam to a same location as the generation beam or another location. The control system 204 may also direct the behavior of the second measuring device. However, various configurations may be envisaged. Further, the above elements may be separate, together or in various combinations, among others.

As such, a system and method for process control of tubing and sheet thickness is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed is:

1. An apparatus for determining and implementing a control action associated with a characteristic of a tube during manufacturing of the tube, the apparatus comprising:
   a first coherent electromagnetic energy source for producing a generator beam of coherent electromagnetic energy, the generator beam impinging the tube and generating a sonic energy signal about the tube;
   a second coherent electromagnetic energy source for producing a measuring beam of coherent electromagnetic energy, the measuring beam impinging the tube and reflecting from the tube as a scattered electromagnetic energy having a modulation associated with the sonic energy signal;
   an interferometer for collecting part of the scattered electromagnetic energy and deriving a signal indicative of the sonic energy signal from the scattered electromagnetic energy;
   an interpreter for determining the characteristic associated with the tube from the signal indicative of the sonic energy signal; and
   a controller for changing movement of the tube in response to a deviation from a desired value range of the characteristic to correct the deviation in the tube to the desired value range.

2. The apparatus of claim 1 wherein the controller alters at least one of a temperature, pressure and torque applied to the tube in response to the deviation.

3. The apparatus of claim 1 wherein the first coherent electromagnetic energy source is a $CO_2$ laser and the second coherent electromagnetic energy source is a ND:YAG laser.

4. The apparatus of claim 1 wherein the characteristic is a thickness of a wall of the tube.

5. The apparatus of claim 1, the apparatus further comprising:
   a mirror, the mirror operable to direct the measuring beam to a particular location on a surface of the tubing.

6. The apparatus of claim 5 wherein the particular location is a same location as that of the impinging generator beam of coherent electromagnetic energy.

7. The apparatus of claim 1 wherein the controller initiates the producing of the generator beam of coherent electromagnetic energy.

8. The apparatus of claim 1 wherein the controller initiates the producing of the measuring beam.

9. The apparatus of claim 1 wherein the interpreter utilizes information associated with a velocity of movement of the tube during manufacturing to determine the characteristic of the tube.

10. A method manufacturing a tube having an axis, the method comprising:
    rotating the tube about the axis and moving the tube axially;
    producing a generator beam of coherent electromagnetic energy with a first coherent electromagnetic energy source, the generator beam impinging the tube and generating a sonic energy signal about the tube;
    producing a measuring beam of coherent electromagnetic energy with a second coherent electromagnetic energy source, the measuring beam impinging the tube and reflecting from the tube as a scattered electromagnetic energy having a modulation associated with the sonic energy signal;
    collecting part of the scattered electromagnetic energy with an interferometer;
    deriving a signal indicative of the sonic energy signal from the scattered electromagnetic energy;
    determining with an interpreter a measured thickness of a wall of the tube from the signal indicative of the sonic energy signal; and
    changing movement of the tube in response to a deviation of the measured thickness of the wall of the tube from a desired value range of the thickness to correct the deviation in the tube to the desired value range.

11. The method of claim 10 further comprising altering at least one of a temperature, pressure and torque applied to the tube in response to the deviation.

12. The method of claim 10 wherein the first coherent electromagnetic energy source is a $CO_2$ laser and the second coherent electromagnetic energy source is an ND:YAG laser.

13. The method of claim 10, the method further comprising: initiating the generator beam of coherent electromagnetic energy with the controller.

14. The method of claim 10, the method further comprising: initiating the measuring beam of coherent electromagnetic energy with the controller.

15. The method of claim 10 wherein the interpreter utilizes information associated with the velocity of the tube to determine the thickness of the wall of the tube.

16. A method for controlling a tube thickness during a manufacturing process, comprising:
    rotating a tube about an axis and moving the tube axially;
    measuring a tube wall thickness, wherein a $CO_2$ laser produces a generator beam of coherent electromagnetic energy that impinges the tube and generates a sonic energy signal about the tube and an ND:YAG laser produces a measuring beam of coherent electromagnetic energy that impinges the tube and reflects scattered electromagnetic energy associated with the sonic energy signal, and the scattered electromagnetic energy is collected with an interferometer and supplied to an analyzer;
    comparing the measured tube wall thickness with a desired tube wall thickness; and
    altering rotational or translational movement of the tube in response to a deviation from a desired tube wall thickness to correct the deviation in the tube to the desired tube wall thickness.

17. The method of claim 16 further comprising initiating the production of the generator beam and the measuring beam with a controller.

18. The method of claim 16 further comprising generating a signal with the interferometer indicative of the sonic energy signal and directing the signal to a controller.

19. The method of claim 17 wherein the controller causes the measuring beam to follow a spot where the generator beam impinges the tube.

* * * * *